United States Patent
Goto et al.

(10) Patent No.: US 9,910,019 B2
(45) Date of Patent: Mar. 6, 2018

(54) PRESSURE CONTROL VALVE AND SUPERCRITICAL FLUID CHROMATOGRAPH

(71) Applicant: SHIMADZU CORPORATION, Kyoto-shi, Kyoto (JP)

(72) Inventors: Hiroomi Goto, Kyoto (JP); Tsunehiro Inoue, Kyoto (JP); Takahiro Mori, Kyoto (JP); Hirohisa Abe, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 92 days.

(21) Appl. No.: 14/914,868

(22) PCT Filed: Sep. 2, 2013

(86) PCT No.: PCT/JP2013/073545
§ 371 (c)(1),
(2) Date: Feb. 26, 2016

(87) PCT Pub. No.: WO2015/029252
PCT Pub. Date: Mar. 5, 2015

(65) Prior Publication Data
US 2016/0209377 A1    Jul. 21, 2016

(51) Int. Cl.
*G01N 30/32*   (2006.01)
*F16K 7/16*   (2006.01)
(Continued)

(52) U.S. Cl.
CPC ............... *G01N 30/32* (2013.01); *F16K 7/16* (2013.01); *F16K 25/005* (2013.01);
(Continued)

(58) Field of Classification Search
CPC ...... G01N 30/32; G01N 30/7233; F16K 7/16; F16K 25/005; F16K 27/0236; F16K 31/004
See application file for complete search history.

(56) References Cited

U.S. PATENT DOCUMENTS 4,070,004 A    1/1978  Friswell
4,558,845 A   12/1985  Hunkapiller
(Continued)

FOREIGN PATENT DOCUMENTS

EP    0 724 901 A1   8/1996
EP    2 317 310 A1   5/2011
(Continued)

OTHER PUBLICATIONS

International Search Report dated Oct. 8, 2013, issued in counterpart Application No. PCT/JP2013/073545 (2 pages).
(Continued)

*Primary Examiner* — David Bolduc
(74) *Attorney, Agent, or Firm* — Westerman, Hattori, Daniels & Adrian, LLP

(57) ABSTRACT

A pressure control valve includes a pressure control block including a bore hole that is bored perpendicularly from one outer surface, and two internal channel openings of whose end portions are at a bottom surface of the bore hole, a valve body having elasticity and covering the bottom surface of the bore hole, a sealing member for pressing a portion of the valve body against the bottom surface of the bore hole, the portion abutting a peripheral edge portion of a portion of the bottom surface where the openings are provided, and an actuator for driving a portion, of the valve body, abutting the portion where the openings are provided in a direction perpendicular to the bottom surface of the bore hole.

12 Claims, 11 Drawing Sheets

(51) Int. Cl.
    F16K 25/00      (2006.01)
    F16K 27/02      (2006.01)
    F16K 31/00      (2006.01)
    G01N 30/72      (2006.01)
    B01D 15/40      (2006.01)

(52) U.S. Cl.
    CPC ........ *F16K 27/0236* (2013.01); *F16K 31/004*
            (2013.01); *G01N 30/7233* (2013.01); *B01D*
            *15/40* (2013.01); *G01N 2030/328* (2013.01)

(56) References Cited

U.S. PATENT DOCUMENTS

| | | | |
|---|---|---|---|
| 5,031,448 A | 7/1991 | Saito | |
| 5,083,742 A | 1/1992 | Wylie et al. | |
| 5,224,510 A | 7/1993 | Pericles | |
| 5,413,311 A | 5/1995 | Arstein et al. | |
| 8,511,643 B2 | 8/2013 | Kamada et al. | |
| 2003/0155541 A1* | 8/2003 | Sheydayi ................. | F16K 7/17 251/61 |
| 2011/0094606 A1* | 4/2011 | Kanomata .............. | B01D 15/40 137/487.5 |
| 2011/0233443 A1* | 9/2011 | Kamada ................ | C22C 19/055 251/331 |

FOREIGN PATENT DOCUMENTS

| | | |
|---|---|---|
| JP | 48-39701 | 11/1973 |
| JP | 48-39701 Y1 | 11/1973 |
| JP | 2-190761 A | 7/1990 |
| JP | 02-190761 A | 7/1990 |
| JP | 3-172688 A | 7/1991 |
| JP | 3-177670 A | 8/1991 |
| JP | 6-66777 A | 3/1994 |
| JP | 06-272770 A | 9/1994 |
| JP | 6-272770 A | 9/1994 |
| JP | 8-338832 A | 12/1996 |
| JP | 2001-500260 A | 1/2001 |
| JP | 2003-49959 A | 2/2003 |
| JP | 2011-202681 A | 10/2011 |
| WO | 98/11431 A1 | 3/1998 |
| WO | 03/071173 A1 | 8/2003 |
| WO | 2008/005838 A2 | 1/2008 |

OTHER PUBLICATIONS

Extended European Search Report dated Feb. 24, 2017, issued in counterpart European Application No. 13892280.2. (9 pages).
Supplementary European Search Report dated Mar. 14, 2017, issued in counterpart European Application 13892280.2. (1 page).
Translation of Office Action dated Aug. 30, 2016, issued in counterpart Japanese Patent Application No. 2015-533919. (7 pages).

* cited by examiner

US 9,910,019 B2

PRESSURE CONTROL VALVE AND SUPERCRITICAL FLUID CHROMATOGRAPH

TECHNICAL FIELD

The present invention relates to a pressure control valve and a supercritical fluid chromatograph that uses the pressure control valve.

BACKGROUND ART

In recent years, supercritical fluid chromatography (hereinafter "SFC") has been gaining attention. The SFC is chromatography that is performed by applying specific temperature and pressure to carbon dioxide or the like to obtain a supercritical fluid, and by using the supercritical fluid as a solvent. The supercritical fluid has properties of both liquid and gas, and is more diffusive but less viscous than liquid. Using such a supercritical fluid as a solvent allows fast, high-separation, high-sensitivity analysis, Generally, to maintain a solvent in a supercritical state, the flow rate has to be a minute flow rate of 3 ml/min or less, and the pressure in a flow system has to be 10 MPa or more. To this end, an SFC device has a pressure control valve for maintaining the flow system at a specific pressure of 10 MPa or more provided at a later stage of an analytical column.

The pressure control valves include those that adopt a method of adjusting a gap (opening area) between a valve seat provided with an inlet channel and a valve body blocking the inlet channel (see Patent Document 1), those that adopt a method of adjusting a channel width (opening area) by driving a diaphragm (see Patent Document 2), those that adopt a method of inserting a needle into an orifice opening at an end of an inlet channel and of adjusting a gap (opening area) based on the insertion depth of the needle into the orifice opening (see Patent Document 3), and the like.

Furthermore, a diaphragm valve may be cited as a general control valve which is not for SFC (see Patent Documents 4 and 5). Generally, a diaphragm valve has an inlet channel arranged at the center of a valve chamber, and controls the pressure by pressing a valve body (diaphragm) against an orifice valve seat of the inlet channel and blocking the inlet channel, and also an outlet is arranged at one position in the periphery. According to this structure, the internal volume of a control chamber is great, and a volume (dead volume) that does not contribute to the flow of a liquid is present on the opposite side of an outlet channel from the inlet channel.

Although it is not a valve for SFC, a pinch valve may be cited as a valve with a small dead volume (see Patent Document 6). The pinch valve controls the pressure by having an inlet tube and an outlet tube inserted to both ends of a deformable valve tube, and by adjusting the opening areas communicating with the inlet tube and the outlet tube by flattening the valve tube. To control the pressure inside a channel of the SFC, a high sealing property is required at insertion portions of an inlet tube and an outlet tube to a valve tube. Since a pressure of 10 MPa or more is sometimes applied inside the channel, and also the inner diameter of the channel is generally 0.3 mm or less so that a mobile phase is made to flow at a minute flow rate of 3 ml/min or less, it is difficult to connect a pipe whose inner diameter is 0.3 mm or less to the valve tube with a high sealing property.

Moreover, as described above, with the SFC, the pressure generally has to be at 10 MP or more in a state where the flow rate of a mobile phase is 3 ml, min or less, and thus, opening/closing control is to be performed in a state where the valve tube is almost completely flattened and the opening area is 0.001 mm$^2$ or less. This may cause a stress to concentrate at the flattened portion of the valve tube, and the valve tube may be damaged. Accordingly, it is difficult to use such a pinch valve for the SEC.

PRIOR ART DOCUMENTS

Patent Documents

Patent Document 1: JP 2 90761 A
Patent Document 2: JP 3-172688 A
Patent Document 3: JP 8-338832 A
Patent Document 4: JP 3-177670 A
Patent Document 5: JP 2011-202681 A
Patent Document 6: JP 2003-49959 A

SUMMARY OF THE INVENTION

Problems to be Solved by the Invention

By connecting a mass spectrometry (MS) to an SFC and realizing a structure of SFC-MS, the detection sensitivity and the identification sensitivity may be increased. In the case of the structure of SFC-MS, the MS is connected to a downstream side of a pressure control valve, and components to be examined, which have been separated in time by a separation column, inevitably pass through the pressure control valve. If a dead volume not included in the flow path of a mobile phase exists in the pressure control valve, the mobile phase stagnates in the dead volume and the components which have been separated in time by the separation column get mixed together, and accurate analysis of the mixed components by the MS is disabled. Accordingly, particularly in the case of the structure of the SFC-MS, t the pressure control valve is desirably structured in such a way that the internal dead volume is made as small as possible so as to prevent the separation performance of the separation column from being impaired.

Accordingly, the present invention has its object to reduce the dead volume inside a pressure control valve for SEC.

Solutions to the Problems

A pressure control valve according to the present invention includes a pressure control block including a bore hole that is bored perpendicularly from one outer surface, and two internal channels openings of whose end portions are at a bottom surface of the bore hole, a valve body having elasticity and covering the bottom surface of the bore hole, a sealing member for pressing a portion of the valve body against the bottom surface of the bore hole, the portion abutting a peripheral edge portion of a portion of the bottom surface where the openings are provided, and an actuator for driving a portion, of the valve body, abutting the portion where the openings are provided in a direction perpendicular to the bottom surface of the bore hole.

According to this pressure control valve, a gap that is formed between the bottom surface of the bore hole and the valve body forms a pressure control space for controlling a pressure, With the pressure control valve of the present invention, the valve body directly contacts a mobile phase under a high pressure, and thus, it is necessary that the valve body has a chemical resistance and a pressure resistance. In addition, with a supercritical fluid chromatograph, carbon dioxide which is a mobile phase may be vaporized due to a steep drop in the pressure and be instantly cooled by the heat of vaporization, thereby generating dry ice. Accordingly, the valve body is desirably made of a resistant material with a chemical resistance, an impact resistance, and a pressure resistance. Then, damage to the valve body by the dry ice may be suppressed, and the durability of the pressure control valve may be increased. As such a resistant material, resin such as polybutylene terephthalate (PBT), polyether ether ketone (PEEK), or ultra high molecular weight polyethylene may be cited.

Further, the valve body may be made from an elastic member having elasticity and a protective film that is present between the elastic member and the bottom surface of the bore hole. The protective film may be made of a resistant material with a chemical resistance, an impact resistance, and a pressure resistance. Also according to such a method, damage to the valve body by dry ice may be suppressed, and the durability of the pressure control valve may be increased.

According to a desirable mode of the pressure control valve of the present invention, the bore hole is formed into a cylindrical shape, the sealing member includes a cylindrical portion that is fitted in the bore hole, and the actuator drives a rod-shaped member that penetrates the cylindrical portion of the sealing member and whose tip end is in contact with a center portion of the valve body.

According to the mode described above, desirably, a thread is formed on an inner circumferential surface of the bore hole, a thread for being engaged with the thread on the inner circumferential surface of the bore hole is formed on an outer circumferential surface of the cylindrical portion of the sealing member, and a position of the cylindrical portion in a depth direction inside the bore hole is changed by rotation of the sealing member. The sealing member may then be attached or detached simply by rotation of the sealing member, and assembly and disassembly of the pressure control valve may be facilitated.

A supercritical fluid chromatograph according to the present invention includes an analysis channel a mobile phase supply section for supplying a mobile phase to the analysis channel, a sample introduction section for introducing a sample into the analysis channel, a separation column that is arranged on the analysis channel, on a downstream side of the sample introduction section, a detector that is arranged on the analysis channel, on a downstream side of the separation column, the detector being for detecting a sample component separated by the separation column, and a pressure control valve of the present invention, the pressure control valve arranged on the analysis channel, on a downstream side of the detector, the pressure control valve being for controlling a pressure inside the analysis channel to a pressure by which the mobile phase is placed in a supercritical state.

Effects of the Invention

According to the pressure control valve of the present invention, a gap that is formed between the bottom surface of the bore hole and the valve body forms a pressure control space for controlling a pressure, and thus, the pressure control space is very small, and almost no dead volume is present. Accordingly, components separated by a separation column of SFC are not mixed inside the pressure control valve, and the separation performance of the separation column is not impaired.

The supercritical fluid chromatograph of the present invention uses the pressure control valve of the present invention to control the pressure inside the analysis channel, and thus, the separation performance of the separation column is not impaired, and accurate separation/analysis may be performed.

EMBODIMENTS OF THE INVENTION

Figure 1:
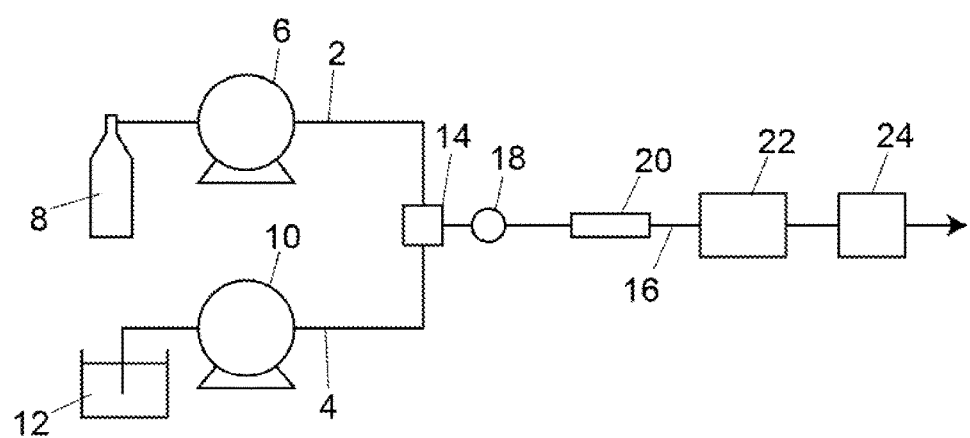
FIG. 1 is a channel diagram schematically showing an example of a supercritical fluid chromatograph.

FIG. 1 is a channel diagram schematically showing an example of a supercritical fluid chromatograph.

A carbon dioxide delivery channel 2 for delivering liquid carbon dioxide by a pump 6 and a methanol delivery channel 4 for delivering methanol, which is a modifier, by a pump 10 are connected to a mixer 14. An analysis channel 16 is connected to the mixer 14. A sample injection section (autosampler) 18 for injecting a sample into the analysis channel 16, a separation column 20, a detector 22, and a pressure control valve 24 are arranged on the analysis channel 16.

Carbon dioxide and methanol are mixed by the mixer 14, and are introduced into the analysis channel 16 as a mobile phase. The carbon dioxide delivery channel 2, the methanol delivery channel 4, and the mixer 14 form a mobile phase delivery section. The internal pressure of the analysis channel 16 is controlled to 10 MPa or more by the pressure control valve 24, and a mobile phase that is introduced into the analysis channel 16 is placed in the state of a supercritical fluid. A sample that is injected by the sample injection section 18 is carried to the separation column 20 by the mobile phase which has turned into a supercritical fluid, and is separated into components and discharged outside via the detector 22 and the pressure control valve 24. Additionally, a mass spectrometry (MS) may be connected to a later stage of the pressure control valve 24.

An example of the pressure control valve 24 will be described with reference to FIGS. 2A and 2B.

The pressure control valve 24 is provided with a pressure control block 30. The material of the pressure control block 30 is a material which is excellent in chemical resistance and pressure resistance, such as stainless steel (SUS316). A bore hole 32 is provided being bored cylindrically and perpendicularly to one outer surface of the pressure control block 30.

Edge portions of opposing side surfaces of the pressure control block 30 are tapered, and pipe connection sections 36a and 36b are provided at respective tapered portions. An end portion of a pipe 40a is fixed to the pipe connection section 36a by a fixing member 42a formed from a ferrule and a male nut In the same manner, an end portion of a pipe 40b is fixed to the pipe connection section 36b by a fixing member 42b formed from a ferrule and a male nut. The inner diameter of the pipes 40a and 40b is, for example, 0.1 mm. A mobile phase flows in through the pipe 40a, and flows out through the pipe 40b.

The pressure control block 30 includes an internal channel 38a that communicates with the pipe connection section 36a, and an internal channel 38b that communicates with the pipe connection section 36b. End portions of the internal channels 38a and 38b reach the center portion of a bottom surface 34 of the bore hole 32, and form two openings 39a and 39b at the bottom surface 34 of the bore hole 32 (see FIG. 2B). The pipes 40a and 40b communicate with the center portion of the bottom surface 34 of the bore hole 32 via the internal channels 38a and 38b, respectively. In the present example, the channels 38a and 38b each form an angle of 60 degrees with an axis that is perpendicular to the surface where the bore hole 32 is provided (the angle formed by the channels 38a and 38b is 120 degrees), and the end portions of the channels 38a and 38b are formed so as to converge at the center portion of the bottom surface 34 of the bore hole 32. The inner diameter of the channels 38a and 38b is, for example, 0.3 mm or less.

A disc-shaped valve body 44 is disposed on the bottom surface 34 of the bore hole 32. The valve body 44 is made of a resistant material with a chemical resistance, an impact resistance, and a pressure resistance. As the resistant material, a resin such as PBT, PEEK or ultra high molecular weight polyethylene may be cited. The valve body 44 covers the entire bottom surface 34 of the bore hole 32, and its peripheral edge portion is pressed toward the bottom surface 34 of the bore hole 32 by a sealing member 46.

The sealing member 46 is a cylindrical member having a through hole at the center portion, and a thread is formed on its outer circumferential surface. A thread for being engaged with the thread on the outer circumferential surface of the sealing member 46 is formed on the inner circumferential surface of the bore hole 32. The sealing member 46 may be moved vertically inside the bore hole 32 by being rotated. A tip end surface, of the sealing member 46, inserted in the bore hole 32 contacts the peripheral edge portion of the valve body 44, and presses the peripheral edge portion of the valve body 44 against the bottom surface 34 of the bore hole 32. The sealing member 46 is formed of a material with certain hardness, such as PEEK resin or stainless steel, in order to press the valve body 44 toward the bore hole 32, and does not have to have a chemical resistance.

A pressing rod 48 penetrates the through hole at the center of the sealing member 46. The inner diameter of the through hole of the sealing member 46 is, for example, about 2 mm and the pressing rod 48 has an outer diameter that is slightly smaller than the inner diameter. A tip end of the pressing rod 48 is in contact with the center portion of the valve body 44. The pressing rod 48 is driven along one direction (vertical direction in the drawing) by an actuator 56. Details of the actuator 56 will be given later.

According to this pressure control valve 24, a small gap is formed between the center portion of the bottom surface 34 of the bore hole 32 and the valve body 44 by a pressure from a mobile phase flowing in from the pipe 40a, and the mobile phase flows through the gap. By controlling the size of the gap between the center portion of the bottom surface 34 of the bore hole 32 and the valve body 44 by the actuator 56, the pressure inside the channel at the upstream side of the pressure control valve 24 is controlled.

With the pressure control valve 24, the height of the gap between the bottom surface 34 of the bore hole 32 and the valve body 44 in a state where the pressure inside the upstream channel is maintained at 10 MPa or more is about several micrometers, and its internal volume is 1 μL or less. Accordingly, the pressure may be controlled with high accuracy in a state where a minute amount of mobile phase is made to flow. Moreover, since the peripheral edge portion of the valve body 44 is sealed by being pressed against the bottom surface 34, there is almost no dead volume to be a stagnation point of the mobile phase.

Figure 2A:
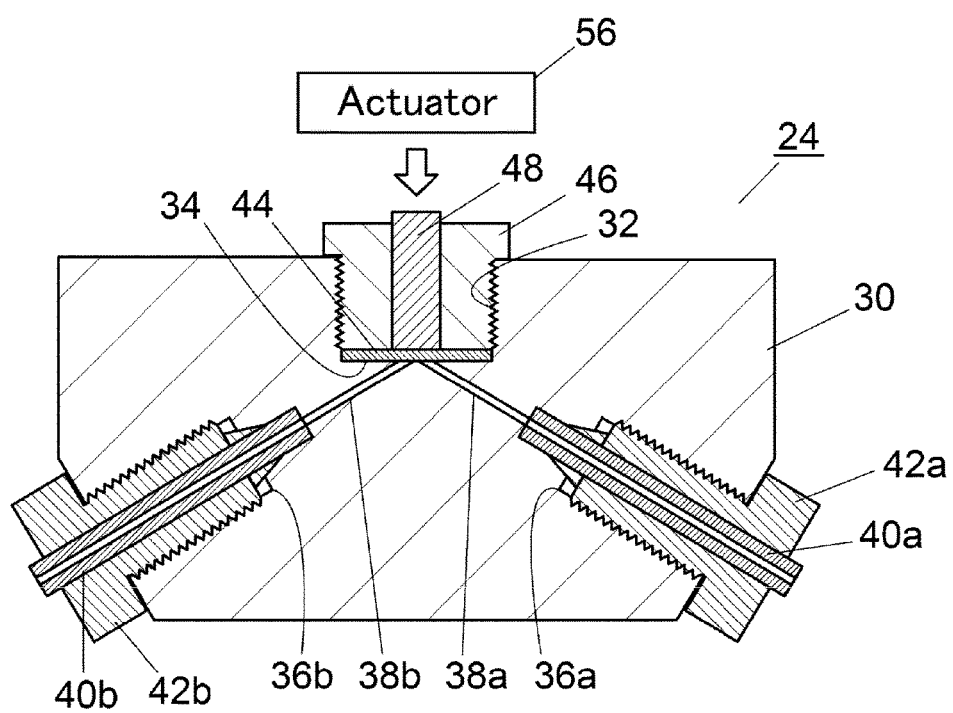
FIG. 2A is a cross-sectional diagram showing an example of a pressure control valve.
Figure 2B:
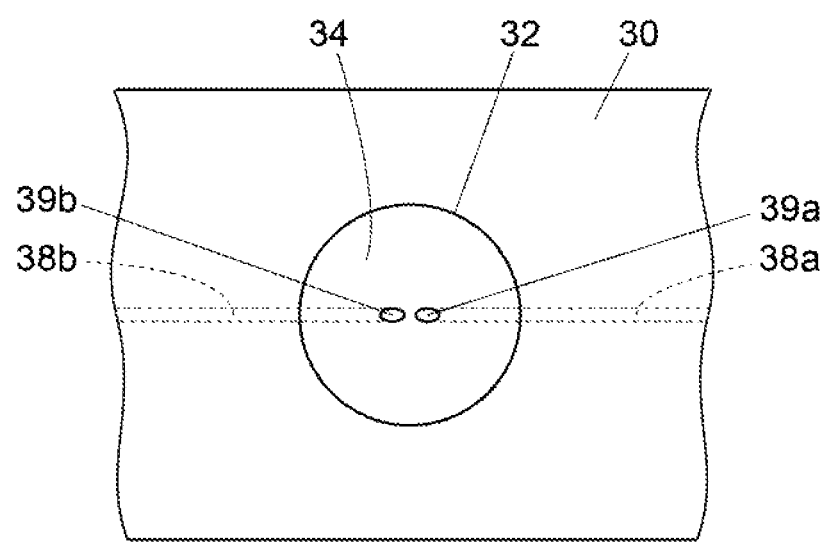
FIG. 2B is a diagram showing, from above, the inside of a bore hole of the pressure control valve of the example.
Figure 3:
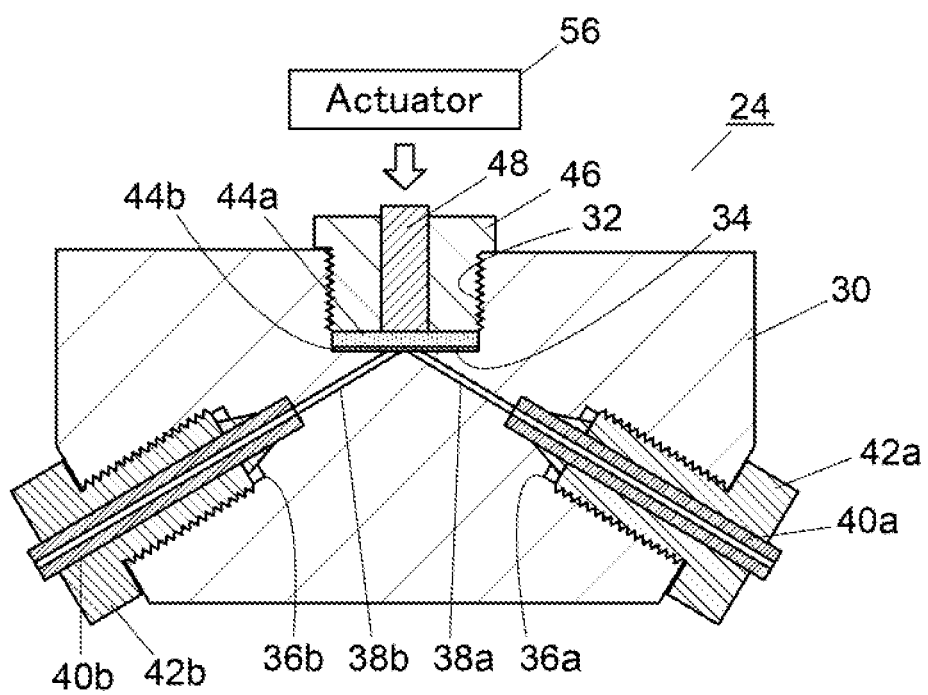
FIG. 3 is a cross-sectional diagram showing another example of the pressure control valve.

As shown in FIG. 3, a valve body formed from an elastic member 44a and a protective film 44b may be used in place of the valve body 44 in FIG. 2A. The elastic member 44a is formed of a rubber material (for example, Viton (registered trademark), Kalrez (registered trademark), Perfluoro (registered trademark)) having more elasticity than the valve body 44 of the example described above, and the protective film 44b is formed of a resistant material with a chemical resistance, an impact resistance, and a pressure resistance. By forming the valve body by a highly elastic rubber material, the proportion of the amount of displacement of the center portion of the valve body to the amount of displacement of the pressing rod 48 is reduced, and the resolution of control of the gap between the center portion of the bottom surface 34 of the bore hole 32 and the valve body may be enhanced.

Figure 4:
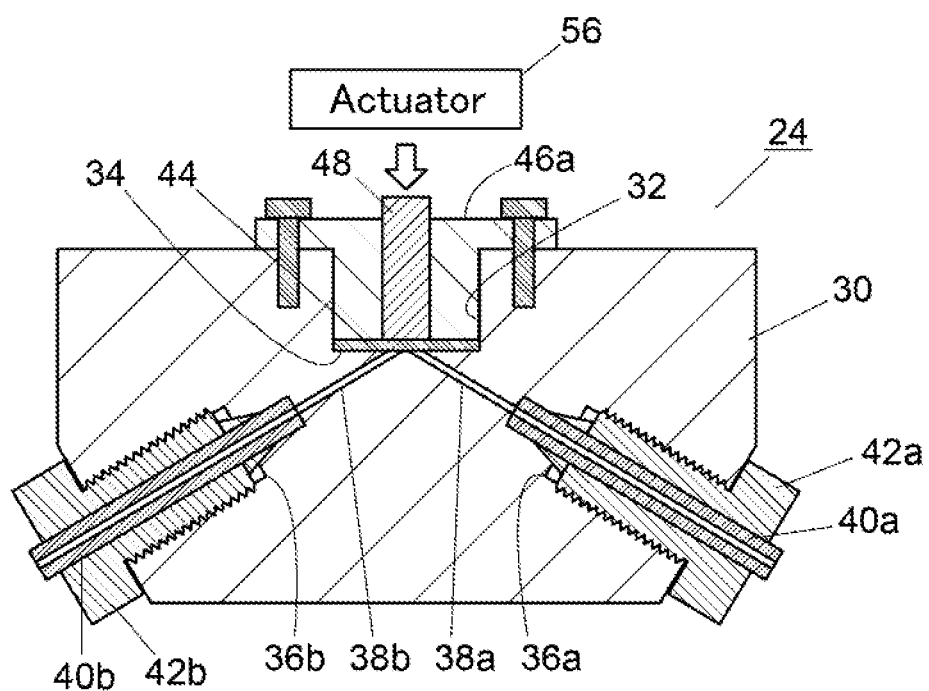
FIG. 4 is a cross-sectional diagram showing another example of the pressure control valve.

In the present example, the force of pressing the peripheral edge portion of the valve body 44 against the bottom surface of the bore hole 32 is adjusted by displacing the sealing member 46 inside the bore hole 32 by rotation of the sealing member 46, but the present invention is not limited to such a configuration. For example, as shown in FIG. 4, a flange portion having a larger outer diameter than the bore hole 32 may be provided at a portion, of a sealing member 46a, which is not inserted in the bore hole 32, and the flange portion may be fixed to the pressure control block 30 by a screw.

Next, an example of the actuator 56 will be described with reference to FIG. 5.

The actuator 56 includes a stepper motor 70 and a piezo element 72. The piezo element 72 is for vertically displacing a displacement section 72a that is arranged vertically downward. The dynamic range of the piezo element 72 is about 10 μm, and the piezo element 72 has a control resolution of nanometers. That is, the position of the displacement section 72a may be controlled in nanometers according to the size of a voltage that is applied between 0 V to 100 V. The tip end of the displacement section 72a contacts a pressing rod 54, and the gap between a recessed section 42 and a protruding section 44b inside the pressure control block 30 may be controlled in nanometers by controlling the applied voltage to the piezo element 72. The piezo element 72, the displacement section 72a, and the pressing rod 54 form a piezoelectric mechanism. The piezo element 72 is held by a piezo holding member 76.

When a positive or negative voltage in one pulse is applied, the stepper motor 70 rotates a bar screw 74 in a forward or reverse direction by the angle corresponding to one step. The piezo holding member 76 is held being engaged with the bar screw 74, and is raised or lowered according to the rotation of the bar screw 74. The stepper motor 70 the bar screw 74, and the piezo holding member 76 form a stepper mechanism.

Here, with respect to the rotation direction of the stepper motor 70, the direction of lowering the piezo holding member 76 is defined as the forward direction, and the direction of raising the piezo holding member 76 is defined as the reverse direction.

Figure 6:
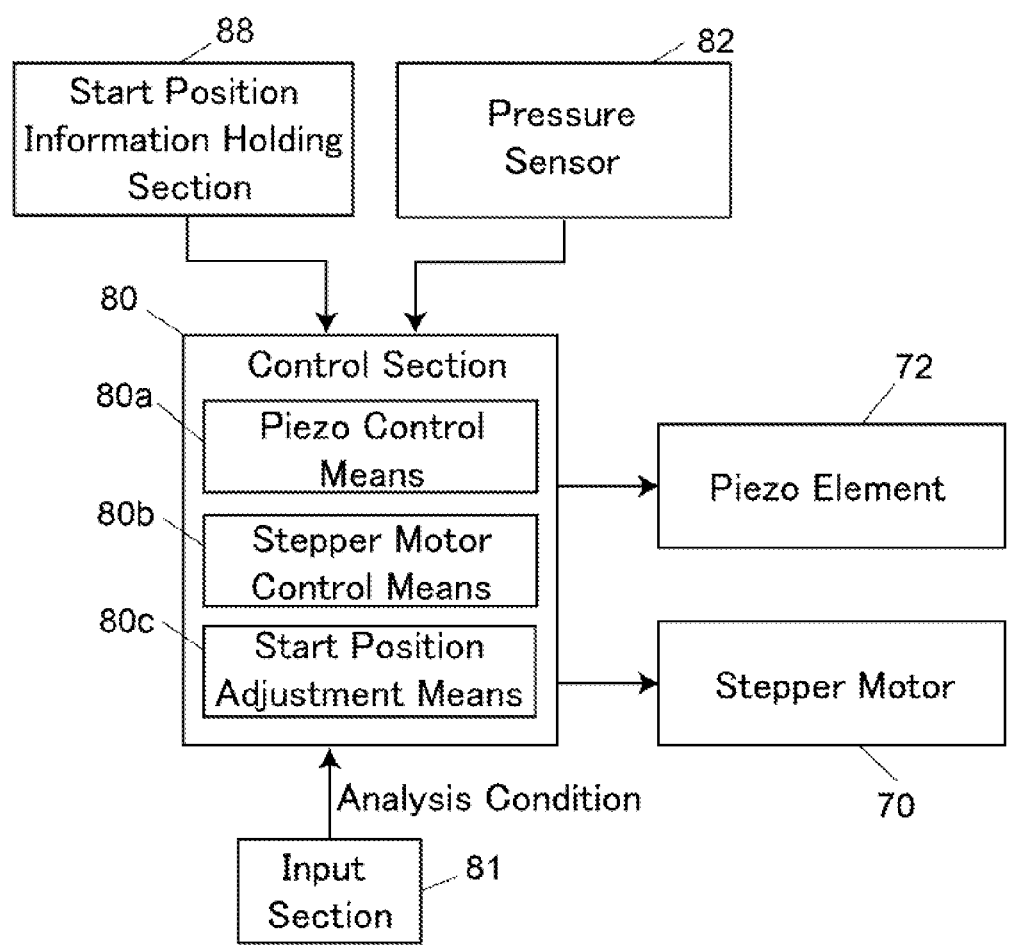
FIG. 6 is a block diagram showing a control system of the actuator in FIG. 5.

A control system of actuator 56 will be described with reference to FIG. 6.

The stepper motor 70 and the piezo element 72 are controlled by a control section 80. Analysis information such as the flow rate of a mobile phase and the pressure inside the analysis channel 16 are set in the control section 80 by an analyst by an input section 81. The control section 80 controls the pressure inside the analysis channel 16 to a set value, based on a pressure value (set value) which has been set. In order to control the stepper motor 70 and the piezo element 72, the control section 80 includes piezo control means 80a, stepper motor control means 80b. and start position adjustment means 80c.

The piezo control means 80a is configured to control an applied voltage to the piezo element 72 in such a way that the pressure inside the analysis channel 16 will be at the set value. Although not shown in FIG. 1, a pressure sensor 82 for measuring the pressure inside the analysis channel 16 is provided, and a measurement value of the pressure sensor 82 is captured into the control section 80. The piezo control means 80a outputs an applied voltage to the piezo element 72 in such a way that the measurement value of the pressure sensor 82 will be at the set value.

Figure 10:
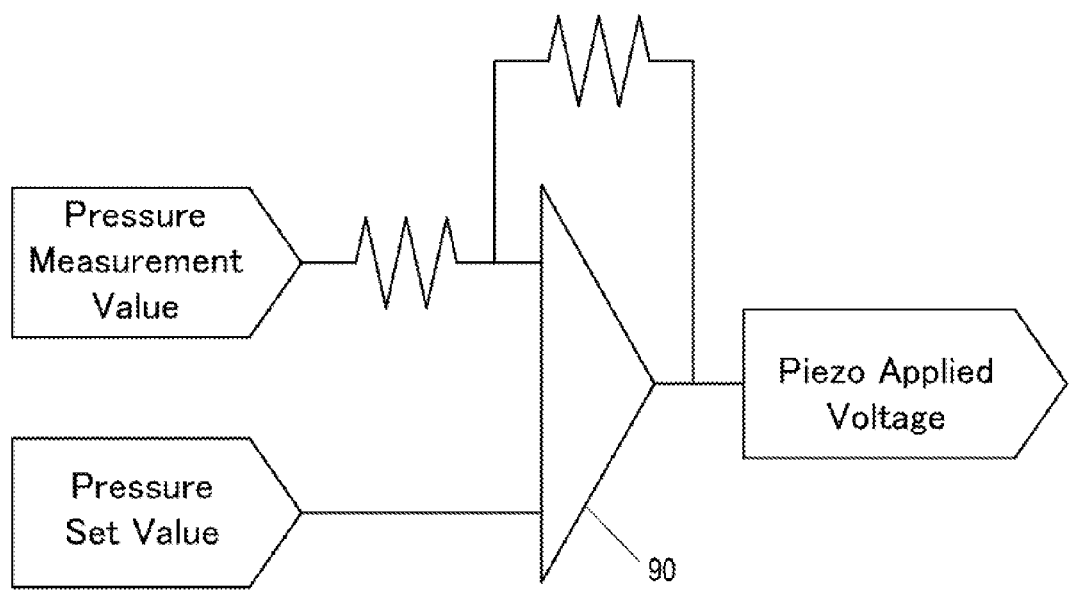
FIG. 10 is a circuit diagram showing an example of a feedback control circuit of the piezo element.

The piezo control means 80a includes a feedback control circuit shown in FIG. 10. The feedback control circuit is configured to input a measurement value of the pressure sensor 82 and the set value to an operational amplifier 90, and to output a value obtained by amplifying the difference by a specific factor as a piezo applied voltage. The piezo applied voltage that is output from the feedback control circuit is captured into the control section 80.

The stepper motor control means 80b is configured to adjust the position of the stepper motor 70 according to the driving state of the piezo element 72. The piezo element 72 is controlled in such a way that a measurement value of the pressure sensor 82 will be at the set value, but if the ambient temperature, the composition of the mobile phase, or the like is changed, the amount of driving of the piezo element 72 that is necessary to cause the measurement value of the pressure sensor 82 to be at the set value may change to outside the dynamic range of the piezo element 72. The stepper motor control means 80b drives the stepper motor 70 when the amount of driving necessary to cause the measurement value of the pressure sensor 82 to be at the set value is about to move out of the dynamic range of the piezo element 72 and changes the position of the piezo element 72 to thereby change the range of the amount of displacement that can be controlled by the piezo element 72.

Whether the stepper motor 70 is to be operated or not is determined based on whether an applied voltage to the piezo element 72 is between an upper limit value (for example, 70 V) and a lower limit value (for example, 30 V) that are set in advance. The stepper motor control means 80b regularly monitors the applied voltage to the piezo element 72, and when the applied voltage to the piezo element 72 is over the upper limit value or below the lower limit value, the stepper motor control means 80b drives the stepper motor 70 and maintains the applied voltage to the piezo element 72 between the upper limit value and the lower limit value at all times.

The start position information adjustment means 80c is configured to adjust the stepper motor 70 to an appropriate start position based on an analysis condition input via the input section 81 and start position information held by a start position information holding section 83. The approximate amount of displacement of the drive section 72a that is necessary to cause the pressure inside the analysis channel 16 to be at a set pressure may be calculated from the analysis condition input via the input section 81, and the appropriate position of the stepper motor 70 (the number of steps in the forward or reverse direction) may be calculated from the calculated amount of displacement of the drive section 72a. Information about a relationship between a set pressure or the flow rate of a mobile phase and the position of the stepper motor 70 is held, as the start position information, by the start position information holding section 88, and the start position information adjustment means 80c calculates the start position of the stepper motor 70 based on the input analysis condition and the start position information in the start position information holding section 80c, and drives the stepper motor 70 to the start position.

Figure 7:
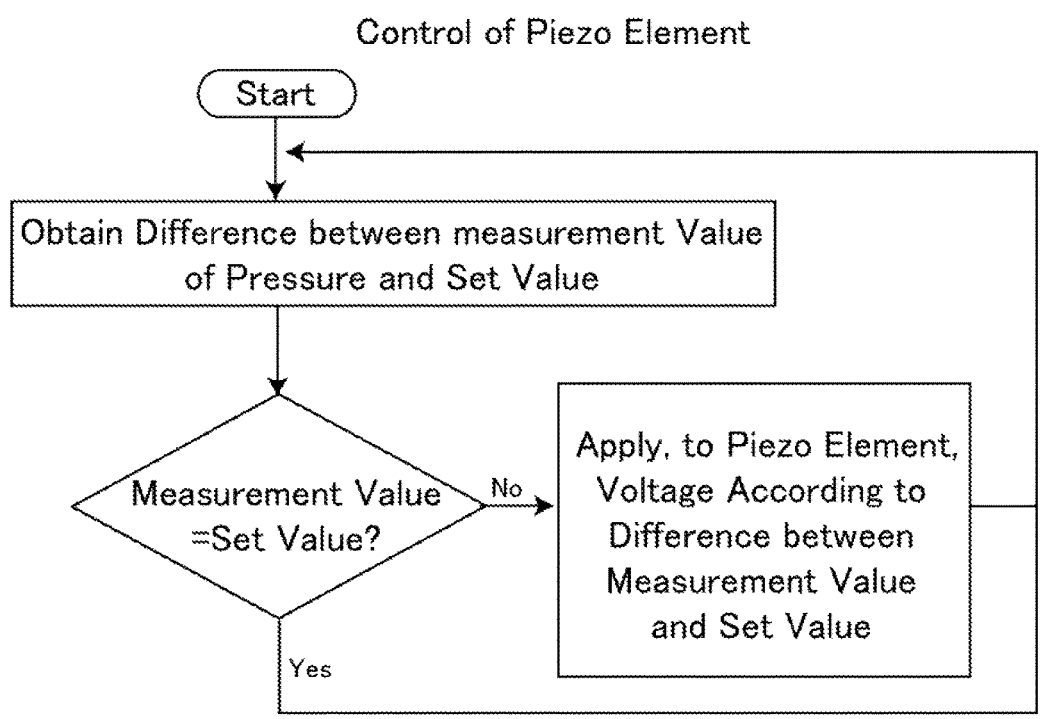
FIG. 7 is a flow hart showing control of a piezo element of the actuator in FIG. 5.

Control of the piezo element 72 will be described with reference to the flow chart in FIG. 7.

The applied voltage to the piezo element 72 is set in such a way that the measurement value of the pressure sensor 82 is equal to the set value. The measurement value of the pressure sensor 82 is captured on a regular basis, and a difference between the captured measurement value of the pressure sensor 82 and the set value is obtained, and a voltage according to the difference is applied to the piezo element 72.

Figure 8:
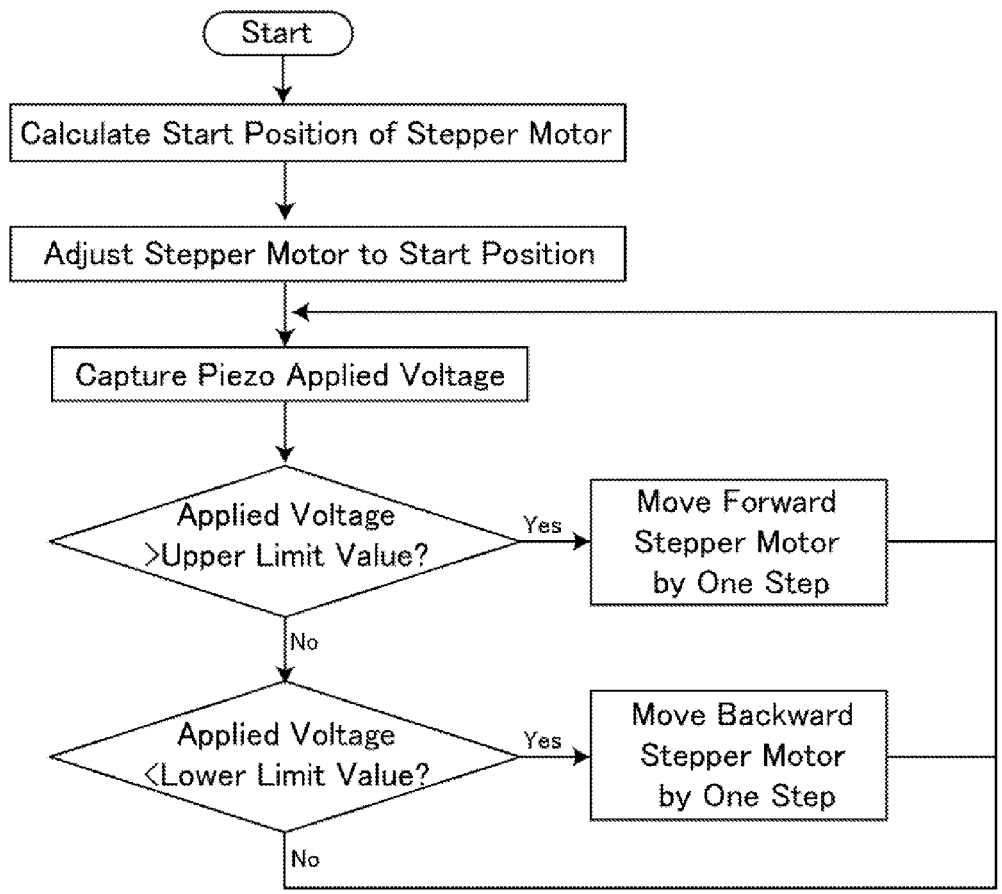
FIG. 8 is a flow chart showing control of a stepper motor of the actuator in FIG. 5.

Control of the stepper motor 70 will be described with reference to the flow chart in FIG. 8.

At the start of analysis, the start position of the stepper motor 70 is calculated based on the analysis condition that is set and the start position information in the start position information holding section 88, and the stepper motor 70 is adjusted to the start position. Then, the applied voltage to the piezo element 72 is captured on a regular basis from a piezo drive section 84. If the captured applied voltage is above the upper limit value, the stepper motor 70 is moved forward by one step (rotated in the forward direction), and if the applied voltage is below the lower limit value, the stepper motor 70 is moved backward by one step (rotated in the reverse direction).

Additionally, if the frequency of control of the stepper motor 70 is not sufficiently less than the frequency of control of the piezo element 72, the stepper motor 70 oscillates to the other side of the normal movable range of the piezo element 72, and thus, control of the stepper motor 70 is desirably performed about once every 10 to 100 msec.

Figure 5:
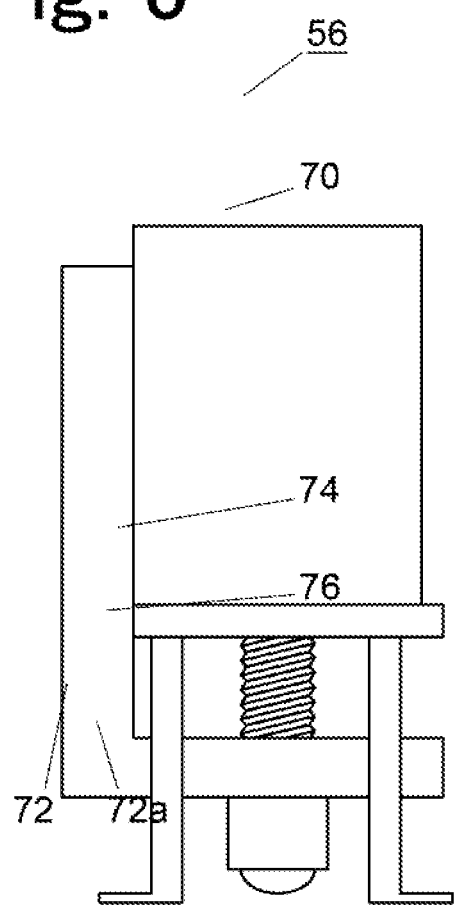
FIG. 5 is a front view showing an example of an actuator used by the pressure control valve.
Figure 9:
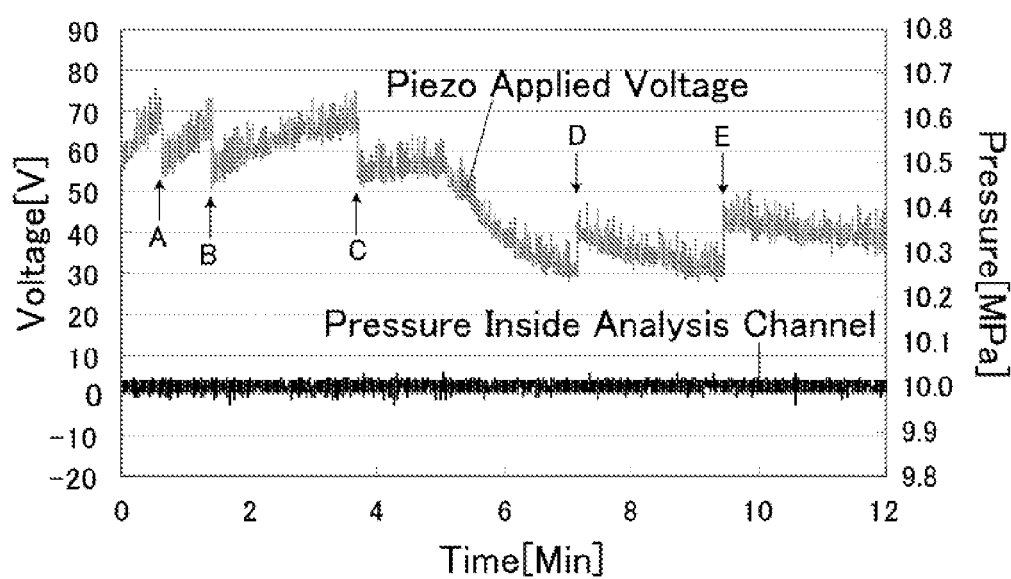
FIG. 9 is a graph showing a change over time in a piezo applied voltage and in the pressure inside an analysis channel.

FIG. 9 shows a change over time in the piezo applied voltage and in the pressure inside the analysis channel at the time of control of the pressure inside the analysis channel of the supercritical fluid chromatograph by the actuator 56 in FIG. 5. Each of points A to E in the drawing indicates a time point of driving of the stepper motor 70. In this measurement, the upper limit value of the piezo applied voltage as the trigger for driving of the stepper motor 70 is set to 70 V. the lower limit value to 30 V, and the pressure inside the analysis channel to 10 MPa.

At points A, B, and C, the piezo applied voltage exceeds 70 V, and thus, the stepper motor 70 is driven by one step in the forward direction, and the piezo element 72 is lowered by 2 µm. Accordingly, the applied voltage to the piezo element 72 necessary to cause the pressure inside the analysis channel to be 10 MPa is reduced. At points D and E, the piezo applied voltage is below 30 V, and thus, the stepper motor 70 is driven by one step in the reverse direction, and the piezo element 72 is raised by 2 µm. Accordingly, the applied voltage to the piezo element 72 necessary to cause the pressure inside the analysis channel to be 10 MPa is increased.

It can be seen from FIG. 9 that the pressure inside the analysis channel is controlled within the range of about ±0.01 MPa with respect to the set pressure 10 MPa. This is because the position of the piezo element 72 is adjusted by the stepper motor 70 according to the applied voltage to the piezo element 72, and the piezo element 72 is thereby constantly driven within the operation range.

DESCRIPTION OF REFERENCE SIGNS

2: Carbon dioxide delivery channel
4: Methanol delivery channel
6, 10: Pump
8: Carbon dioxide
12: Methanol (modifier)
14: Mixer
16: Analysis channel
18: Sample injection section
20: Separation column
22: Detector
24: Pressure control valve
30: Pressure control block
32: Bore hole
34: Bore hole bottom surface
36*a*, 36*b*: Pipe connection section
38*a*, 38*b*: Internal channel
40*a*, 40*b*: Pipe
42*a*, 42*b*: Fixing member
44: valve body
46, 46*a*: Sealing member
48: Pressing rod
56: Actuator
70: Stepper motor
72: Piezo element
72*a*: Displacement section
74: Bar screw
76: Piezo element holding section
80: Control section
80*a*: Piezo control means
80*b*: Stepper motor control means
80*c*: Start position adjustment means
81: Input section
82: Pressure sensor
88: Start position information holding section
90: Operational amplifier

What is claimed is:

1. A pressure control valve comprising:
a pressure control block including a bore hole being bored perpendicularly from one outer surface and having a flat bottom surface, and two internal channels openings of whose end portions are located adjacently to each other at the center portion of the bottom surface of the bore hole;
a plate valve body having elasticity and covering the bottom surface of the bore hole;
a sealing member for pressing a peripheral portion of the valve body against a peripheral edge portion of the bottom surface; and
an actuator for driving the center portion of the valve body in a direction perpendicular to the bottom surface of the bore hole; wherein one of the two internal channels is an inlet channel and another of the two internal channels is an outlet channel; and
wherein the two internal channels are inclined to each other so that the end portions of the two internal channels converge at the center portion of the bottom surface of the bore hole.

2. The pressure control valve according to claim 1, wherein the valve body is made of a resistant material with a chemical resistance, an impact resistance, and a pressure resistance.

3. The pressure control valve according to claim 1, wherein the valve body is made from an elastic member having elasticity and a protective film that is present between the elastic member and the bottom surface of the bore hole, and the protective film is made of a resistant material with a chemical resistance, an impact resistance, and a pressure resistance.

4. The pressure control valve according to claim 1,
wherein the bore hole is formed into a cylindrical shape,
wherein the sealing member includes a cylindrical portion that is fitted in the bore hole, and
wherein the actuator drives a rod-shaped member that penetrates the cylindrical portion of the sealing member and whose tip end is in contact with a center portion of the valve body.

5. The pressure control valve according to claim 4, wherein a thread is formed on an inner circumferential surface of the bore hole, a thread for being engaged with the thread on the inner circumferential surface of the bore hole is formed on an outer circumferential surface of the cylindrical portion of the sealing member, and a position of the cylindrical portion in a depth direction inside the bore hole is changed by rotation of the sealing member.

6. A supercritical fluid chromatograph comprising:
an analysis channel;
a mobile phase delivery section for delivering a mobile phase into the analysis channel;
a sample introduction section for introducing a sample into the analysis channel;
a separation column that is arranged on the analysis channel, on a downstream side of the sample introduction section;
a detector that is arranged on the analysis channel, on a downstream side of the separation column, the detector being for detecting a sample component separated by the separation column; and
a pressure control valve according to claim 1, the pressure control valve being arranged on the analysis channel, on a downstream side of the detector, the pressure control valve being for controlling a pressure inside the analysis channel to a pressure by which the mobile phase is placed in a supercritical state.

7. The supercritical fluid chromatograph according to claim 6, wherein the valve body is made of a resistant material with a chemical resistance, an impact resistance, and a pressure resistance.

8. The supercritical fluid chromatograph according to claim 6, wherein the valve body is made from an elastic member having elasticity and a protective film that is present between the elastic member and the bottom surface of the bore hole, and the protective film is made of a resistant material with a chemical resistance, an impact resistance, and a pressure resistance.

9. The supercritical fluid chromatograph according to claim 6,
wherein the bore hole is formed into a cylindrical shape,
wherein the sealing member includes a cylindrical portion that is fitted in the bore hole, and
wherein the actuator drives a rod-shaped member that penetrates the cylindrical portion of the sealing member and whose tip end is in contact with a center portion of the valve body.

10. The supercritical fluid chromatograph according to claim 9,
wherein a thread is formed on an inner circumferential surface of the bore hole, a thread for being engaged with the thread on the inner circumferential surface of the bore hole is formed on an outer circumferential surface of the cylindrical portion of the sealing member, and a position of the cylindrical portion in a depth direction inside the bore hole is changed by rotation of the sealing member.

11. The pressure control valve according to claim 1, wherein the valve body is disc-shaped.

12. The supercritical fluid chromatograph according to claim 6, wherein the valve body is disc-shaped.

* * * * *